(12) United States Patent
Fabian et al.

(10) Patent No.: US 7,271,302 B1
(45) Date of Patent: Sep. 18, 2007

(54) METHOD FOR BROMINATING ORGANIC COMPOUNDS

(75) Inventors: Kai Fabian, Wilhelmsfeld (DE); Joeran Stoldt, Weiterstadt (DE); Hanns Wurziger, Darmstadt (DE); Norbert Schwesinger, Eching (DE)

(73) Assignee: Merck Patent Gesellschaft, Darmstadt (DE)

( * ) Notice: Subject to any disclaimer, the term of this patent is extended or adjusted under 35 U.S.C. 154(b) by 44 days.

(21) Appl. No.: 10/089,223

(22) PCT Filed: Sep. 19, 2000

(86) PCT No.: PCT/EP00/09155

§ 371 (c)(1),
(2), (4) Date: Sep. 17, 2002

(87) PCT Pub. No.: WO01/23329

PCT Pub. Date: Apr. 5, 2001

(30) Foreign Application Priority Data

Sep. 28, 1999 (DE) .............................. 199 46 367

(51) Int. Cl.
*C07C 25/02* (2006.01)
*C07C 25/125* (2006.01)
*C07C 23/02* (2006.01)
*C07C 23/18* (2006.01)

(52) U.S. Cl. ...................... 570/196; 570/190; 570/191; 570/192; 570/197

(58) Field of Classification Search ................ 570/190, 570/191, 192, 196, 197
See application file for complete search history.

(56) References Cited

FOREIGN PATENT DOCUMENTS

WO        WO9630113 A     10/1996
WO        WO9922857 A     5/1999

OTHER PUBLICATIONS

Bitner et al., Lipids, vol. 5(8), 1970, pp. 707-712.*

* cited by examiner

*Primary Examiner*—Elvis O. Price
(74) *Attorney, Agent, or Firm*—Millen, White, Zelano & Branigan, P.C.

(57) ABSTRACT

The present invention relates to processes for the bromination of organic compounds, and to bromination microreactors for carrying out these processes.

20 Claims, No Drawings

METHOD FOR BROMINATING ORGANIC COMPOUNDS

The present invention relates to processes for the bromination of organic compounds, and to bromination microreactors for carrying out these processes.

The bromination of organic compounds is a process which is carried out very often in the chemical industry and whose great importance is also reflected in numerous publications on this subject.

However, performance of brominations on an industrial scale is associated with safety problems and risks. Firstly, use is frequently made of highly toxic chemical substances which even on their own represent a considerable risk to people and the environment, and secondly brominations often proceed very highly exothermically, and consequently there is an increased risk of explosion when these reactions are carried out on an industrial scale. The procurement of official approval in accordance with the German Federal Emissions Protection Act (BGBI) I No. 71 of 26.10.1998, p. 3178) for the operation of plants for the bromination of organic compounds on an industrial scale is therefore associated with considerable effort.

The object of the present invention was therefore to provide a novel process for the bromination of organic compounds which can be carried out in a simple, reproducible manner with increased safety for people and the environment and with good yields. A further object was to provide an apparatus for carrying out this process.

This object was achieved in accordance with the invention by the provision of novel processes for the bromination of organic compounds in which the organic compound in liquid or dissolved form is mixed with a brominating reagent in liquid or dissolved form, if desired in the presence of a catalyst in liquid or dissolved form in at least one microreactor and reacted for a residence time, and the brominated organic compound is isolated from the reaction mixture.

For the purposes of the invention, a microreactor is taken to mean a reactor having a volume of $\leq 100$ μl in which the liquids and/or solutions are mixed intimately at least once. The volume of the microreactor is preferably $\leq 10$ μl, particularly preferably $\leq 1$ μl. A microreactor is preferably made from thin silicon structures bonded to one another.

The microreactor is preferably a miniaturised flow reactor, particularly preferably a static micromixer. The microreactor is very particularly preferably a static micromixer as described in WO 96/30113, which is hereby introduced by way of reference and is regarded as part of the disclosure.

A microreactor of this type preferably has small channels in which liquids and/or chemical compounds in the form of solutions are preferably mixed with one another due to the kinetic energy of the flowing liquids and/or solutions.

The channels of the microreactor preferably have a diameter of from 10 to 1000 μm, particularly preferably from 20 to 800 μm and very particularly preferably from 30 μm to 400 μm.

The liquids and/or solutions are preferably pumped into the microreactor in such a way that they flow through the latter at a flow rate of from 0.1 μl/min to 10 ml/min, particularly preferably from 1 μl/min to 1 ml/min.

In accordance with the invention, the microreactor is preferably heatable.

For the purposes of the invention, the residence time is taken to mean the time between mixing of the organic compounds, any catalysts and brominating reagents or solutions thereof and work-up of this reaction solution for analysis or isolation of the desired product(s).

The residence time necessary in the processes according to the invention depends on various parameters, such as, for example, the reactivity of the organic compounds, catalysts and brominating reagents employed, the desired degree of bromination or the temperature. It is possible for the person skilled in the art to match the residence time to these parameters and thus to achieve an optimum course of the reaction. The residence time of the reaction solution in the microreactor, where appropriate in the microreactor and the residence zone, is preferably $\leq 3$ hours, in particular $\leq 1$ hour.

In accordance with the invention, the microreactor is preferably connected to at least one residence zone, preferably a capillary, particularly preferably a heatable capillary, via an outlet. After they have mixed in the microreactor, the liquids and/or solutions are passed into this residence zone or capillary in order to extend their residence time.

The reaction mixture is likewise preferably passed through two or more micro-reactors connected in parallel or in series. This achieves an extension of the residence time, even at an increased flow rate, and the bromination reaction components employed are converted virtually completely into the brominated organic compound(s) desired.

In a further preferred embodiment of the process according to the invention, the number and/or arrangement of the channels in one or more micro-reactor(s) are varied in such a way that the residence zone is extended, again resulting in virtually complete conversion into the desired brominated organic compound(s) at an increased flow rate.

The residence time of the reaction solution in the system employed comprising at least one microreactor and, if desired, a residence zone can also be set through the choice of the flow rates of the liquids and/or solutions employed.

The processes according to the invention can be carried out in a very broad temperature range, which is essentially restricted by the temperature resistance of the materials employed for the construction of the microreactor, any residence zone and further constituents, such as, for example, connections and seals, and by the physical properties of the solutions and/or liquids employed. The processes according to the invention are preferably carried out at a temperature of from −90 to +150° C., particularly preferably from −20 to +40° C., very particularly preferably from −10 to +20° C.

The processes according to the invention can be carried out either continuously or batchwise. They are preferably carried out continuously.

For carrying out the processes according to the invention for the bromination of organic compounds, it is necessary for the bromination reaction to be carried out in the homogeneous liquid phase, since otherwise the channels present in the microreactors become blocked.

The course of the bromination reaction in the processes according to the invention can be monitored using various analytical methods known to the person skilled in the art and where appropriate regulated. The course of the reaction is preferably monitored by chromatography, particularly preferably by gas chromatography, and where appropriate regulated.

The brominated organic compounds can likewise be isolated by various methods known to the person skilled in the art. The brominated product(s) is (are) preferably isolated from the reaction mixture by extraction, preferably with an organic solvent, or by precipitation, preferably with an organic solvent and/or water, particularly preferably with water.

Organic compounds which can be employed in the processes according to the invention are all organic compounds which are known to the person skilled in the art as substrates of bromination reactions.

The organic compounds employed are preferably aromatic or heteroaromatic compounds. These aromatic or heteroaromatic compounds include both monocyclic and polycyclic compounds, as well as compounds which have a monocyclic and/or polycyclic, homo- or heteroaromatic basic structure or part-structure, for example in the form of substituents. The term "organic compounds" is also taken to include organometallic compounds whose organic moieties are susceptible to bromination.

The organic compounds employed are likewise preferably aldehydes or ketones which have at least one hydrogen atom in the α-position to the carbonyl group, and unsaturated aliphatic compounds.

The aromatic compounds employed are particularly preferably alkylated aromatic compounds, very particularly preferably toluene, xylene or mesitylene, benzene, naphthalene, azulene, anthracene, phenanthrene, pyrene, fluorene, quinones, such as, for example, ortho- and para-benzoquinone, naphthoquinones, fluorenones, anthrones, phenanthrones, anthraquinones and/or derivatives thereof.

The heteroaromatic compounds employed are particularly preferably oxygen-containing, heteroaromatic compounds and/or derivatives thereof, very particularly preferably furans, such as, for example, benzo-fused furans, dibenzofurans, dibenzodioxanes, pyrylium cations or benzopyranones. Particular preference is likewise given to nitrogen-containing, heteroaromatic compounds and/or derivatives thereof, such as, for example, pyrroles, pyrazoles, imidazoles, triazoles, tetrazoles, pyridines, pyrazines, pyrimidines, pyridinium salts, triazines, tetrazines, pyridine N-oxides, benzo-fused pyrroles, such as, for example, indoles, carbazoles, benzimidazoles or benzotriazoles, phenazine, quinolines, isoquinolines, cinnolines, quinazolines, quinazolines, phenanthroline, bipyridyls and higher homologues thereof, acridines, acridones, and/or pyrene. Particular preference is furthermore given to sulfur-containing, heteroaromatic compounds and/or derivatives thereof, such as, for example, thiophenes, benzo-fused thiophenes, in particular benzothiophenes or dibenzothiophenes, and acenaphthylenes, thiazoles, isothiazoles, biphenylenes, purines, benzothiadiazoles, oxazoles and/or isoxazoles.

Brominating reagents which can be employed in the processes according to the invention are all brominating reagents known to the person skilled in the art. The brominating reagents employed are preferably elemental bromine, dibromoisocyanuric acid, N-bromosuccinimide, hypobromous acid, organic hypobromites, particularly preferably trifluoroacetyl hypobromite, N-bromoacetamide, N-bromophthalimide, pyridinium perbromide and/or dioxane dibromide.

It is essential for the processes according to the invention that the organic compounds, alkylating reagents and any catalysts employed are either themselves liquid or are in dissolved form. If these compounds are not already in liquid form themselves, they must therefore be dissolved in a suitable solvent before the processes according to the invention are carried out. The solvents employed are preferably halogenated hydrocarbons, particularly preferably dichloromethane, chloroform, tetrachloromethane or tetrachloroethane, esters, particularly preferably ethyl acetate, ethers, particularly preferably tetrahydrofuran, diethyl ether or tert-butyl methyl ether, carboxylic acids, particularly preferably acetic acid, or mixtures thereof.

The molar ratio in the processes according to the invention between the organic compound and the brominating reagent employed depends firstly on the reactivity of the organic compounds, catalysts and brominating reagents employed, and secondly on the desired degree of bromination. The degree of bromination itself depends on a number of parameters in addition to the concentration of the reagents employed, such as, for example, temperature, type of catalyst or residence time. It is possible for the person skilled in the art to match the various parameters to the respective bromination reaction in such a way that the desired mono- or polybrominated compound is obtained.

Depending on the reactivity of the organic compounds and brominating reagents employed, it may be advantageous and in some cases even necessary to employ catalysts in the process according to the invention in order to increase the rate of the bromination reaction. The catalysts employed are preferably elemental iodine, mineral acids, particularly preferably sulfuric acid or nitric acid, and/or Lewis acids, particularly preferably aluminium halides, iron halides, zinc halides or antimony halides.

The amount of catalyst employed in the process according to the invention is preferably between 0.1 and 100 mol %, particularly preferably between 1 and 10 mol %, based on the amount of organic compound employed.

The invention furthermore relates to an bromination microreactor for carrying out the process according to the invention. This bromination microreactor has at least one mixing element and, if desired, a residence zone, and its volume, without the volume of the residence zone, is ≦100 μl, preferably ≦10 μl, particularly preferably ≦1 μl.

In a preferred embodiment, the bromination microreactor is a static micro-mixer.

In a further preferred embodiment of the bromination microreactor, it has a residence zone which is a capillary which is preferably connected to an outlet of the bromination microreactor. The capillary is preferably a heatable capillary.

The bromination microreactor is likewise preferably itself heatable.

In the processes according to the invention, the risk to people and the environment due to released chemicals is considerably reduced. Furthermore, the risk of an explosion in the very highly exothermic bromination reactions is reduced, inter alia due to improved mass and heat transport compared with conventional systems. Official approval in accordance with the German Federal Emissions Protection Act (BGBI. I No. 71 of 26.10.1998, p. 3178) for the operation of plants for carrying out the processes according to the invention is therefore easier to obtain. It is also particularly advantageous that the process according to the invention can be carried out continuously. This enables them to be carried out more quickly and at lower cost than conventional processes, and it is possible to prepare any desired amounts of the brominated organic compounds without major measurement and control effort. The course of the bromination reaction can be regulated very quickly in the processes according to the invention. The bromination of organic compounds by the processes according to the invention also enables better control via the reaction duration and reaction temperature than is possible in the conventional processes. The temperature can be selected individually and kept constant in each volume element of the system. The brominated organic products can thus be obtained in very good and reproducible yields.

The invention is explained below with reference to examples. These examples serve merely to explain the invention and do not restrict the general inventive idea.

EXAMPLES

Example 1

Bromination of Mesitylene Using Elemental Bromine:

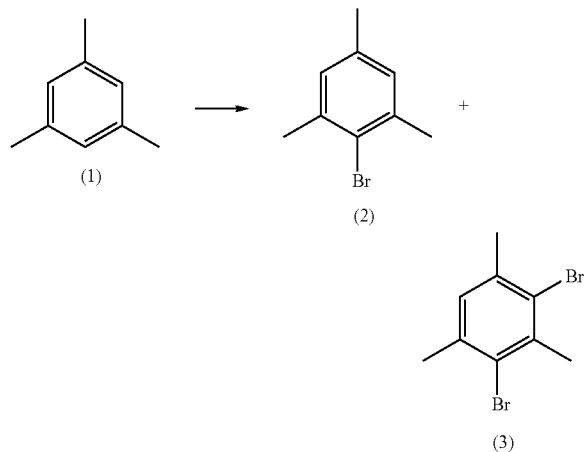

The bromination of mesitylene (1) using elemental bromine was carried out in a static micromixer (Technical University of Ilmenau, Faculty of Machine Construction, Dr. -Ing. Norbert Schwesinger, P.O. Box 100565, D-98684, Ilmenau) having a physical size of 0.8 mm×0.8 mm×0.6 mm and a total volume of 0.125 µl and a total pressure loss of about 1000 Pa. The static micromixer was connected to a Teflon capillary having an internal diameter of 0.25 mm and a length of 1 m via an outlet and an Omnifit medium-pressure HPLC connector (Omnifit, Germany). The temperatures of the static micro-mixer and the Teflon capillary were regulated in an water-filled jacketed vessel thermostatted to 10° C.

In order to prepare a solution of mesitylene, 1.2 g (0.01 mol) of mesitylene were diluted with tetrachloromethane to a total volume of 2 ml. In order to prepare a solution of elemental bromine, 1.7 g (0.011 mol) of bromine were diluted with tetrachloromethane to a total volume of 2 ml. The two solutions were subsequently transferred into the static micromixer using a metering pump (Harvard Apparatus Inc., Pump 22, South Natick, Mass., USA) and 2 ml polypropylene syringes (B. Braun Melsungen AG, Germany). The flow rate here was set to 10 ml/min. The mixed reaction solution was subsequently passed into 2 ml of an HPLC buffer solution comprising acetonitrile and 1% trifluoroacetic acid in the ratio 1:1 (Merck, Darmstadt) in order to terminate the bromination reaction. The reaction mixture was evaluated by combined GC/MS analysis. The reaction mixture comprised 88 area-% of the chromatogram of the monobrominated product (2), 9 area-% of the dibrominated product (3) and 3 area-% of the unbrominated mesitylene (1).

In order to determine the preparative yield of the brominated reaction products, the mixed reaction solution was stirred into a beaker containing 50 ml of water. The system comprising static micromixer and Teflon capillary was subsequently rinsed firstly with 10 ml of water and subsequently with 10 ml of dichloromethane. The combined liquid phases were then stirred for 20 minutes and subsequently extracted three times with 20 ml of diethyl ether each time. The combined ethereal extracts were dried over magnesium sulfate and freed from solvent under reduced pressure, giving 1.7 g (corresponding to 73% of the theoretical yield) of a brownish oil, whose content of monobrominated product (2) was determined by combined GC/MS analysis as 85 area-% of the chromatogram.

Example 2

The set-up and performance were as in Example 1, but the flow rate was set to 20 µl/min. Combined GC/MS analysis of the reaction mixture obtained in this way gave a composition of 51 area-% of the chromatogram of the monobrominated product (2), 47 area-% of the dibrominated product (3) and 2 area-% of mesitylene brominated in the methyl side chain.

The invention claimed is:

1. A process for brominating an organic compound, comprising mixing an organic compound in liquid or dissolved form with a brominating reagent in liquid or dissolved form, optionally in the presence of a catalyst in liquid or dissolved form, in at least one microreactor which has channels having a diameter of 10 to 1000 µm, and reacting for a residence time, and isolating the resultant brominated organic compound from the reaction mixture.

2. A process according to claim 1, wherein the microreactor is a miniaturized flow reactor.

3. A process according to claim 1, wherein the microreactor is a static micromixer.

4. A process for brominating an organic compound, comprising mixing an organic compound in liquid or dissolved form with a brominating reagent in liquid or dissolved form, optionally in the presence of a catalyst in liquid or dissolved form, in at least one microreactor connected to a capillary via an outlet, and reacting for a residence time, and isolating the resultant brominated organic compound from the reaction mixture.

5. A process for brominating an organic compound, comprising mixing an organic compound in liquid or dissolved form with a brominating reagent in liquid or dissolved form, optionally in the presence of a catalyst in liquid or dissolved form, in at least one microreactor with a volume of ≦10 µl, and reacting for a residence time, and isolating the resultant brominated organic compound from the reaction mixture.

6. A process according to claim 1, wherein the microreactor is heatable.

7. A process according to claim 1, wherein the resultant mixture flows through the microreactor at a flow rate of 0.1 µm/min to 10 ml/min.

8. A process according to claim 1, wherein the residence time of the resultant mixture in the microreactor, or in the microreactor and the capillaries, is ≦3 hours.

9. A process according to claim 1, which is carried out at a temperature of −90 to +150° C.

10. A process according to claim 1, wherein the course of the reaction is monitored by chromatography and optionally regulated.

11. A process according to claim 1, wherein the brominated compound is isolated from the reaction mixture by extraction or precipitation.

12. A process according to claim 1, wherein the brominating reagent is elemental bromine, dibromoisocyanuric acid, N-bromosuccinimde, hypobromous acid, organic hypobromites, preferably trifluoroacetyl hypobromite, N-bromoacetamide, N-bromophthalimide, pyridinium perbromide and/or dioxane dibromide.

13. A process according to claim 1, wherein a catalyst is present, which catalyst is iodine, a mineral acid, and/or a Lewis acid.

14. A process according to claim 1, wherein between 0.1 and 100 mol % of, catalyst is present, based on the amount of organic compound.

15. A process according to claim 4, wherein the capillary is heatable.

16. A process according to claim 5, wherein the volume of the microreactor is $\leq 1$ μl.

17. A process according to claim 1, wherein the channels have a diameter of 20 to 800 μm.

18. A process according to claim 1, wherein the channels have a diameter of 30 to 400 μm.

19. A process according to claim 1, wherein a catalyst is present, which catalyst is iodine, sulphuric acid, nitric acid, an aluminum halide, iron halide, zinc halide or antimony halide.

20. A process according to claim 1, wherein the microreactor has a volume of $\leq 10$ μl and/or is connected to a capillary via an outlet.

\* \* \* \* \*